(12) United States Patent
Cotton

(10) Patent No.: US 9,958,361 B2
(45) Date of Patent: May 1, 2018

(54) TEST DEVICE AND METHODS OF USE

(75) Inventor: Paul William Cotton, Halstead Essex (GB)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 496 days.

(21) Appl. No.: 14/126,619

(22) PCT Filed: Jun. 7, 2012

(86) PCT No.: PCT/US2012/041279
§ 371 (c)(1),
(2), (4) Date: Dec. 16, 2013

(87) PCT Pub. No.: WO2012/173856
PCT Pub. Date: Dec. 20, 2012

(65) Prior Publication Data
US 2014/0134750 A1    May 15, 2014

Related U.S. Application Data

(60) Provisional application No. 61/498,076, filed on Jun. 17, 2011.

(51) Int. Cl.
| | | |
|---|---|---|
| *G01N 1/00* | (2006.01) | |
| *G01N 1/28* | (2006.01) | |
| *G01N 33/52* | (2006.01) | |
| *G01N 33/49* | (2006.01) | |
| *G01N 33/493* | (2006.01) | |

(52) U.S. Cl.
CPC ............. *G01N 1/28* (2013.01); *G01N 33/521* (2013.01); *G01N 33/49* (2013.01); *G01N 33/493* (2013.01); *Y10T 436/2575* (2015.01)

(58) Field of Classification Search
CPC ......................................................... G01N 1/28
USPC ......................................................... 436/180
See application file for complete search history.

(56) References Cited

U.S. PATENT DOCUMENTS

| | | | | |
|---|---|---|---|---|
| 4,618,475 | A | | 10/1986 | Wang |
| 4,978,503 | A | * | 12/1990 | Shanks ................. G01N 21/03 156/61 |
| 5,008,077 | A | * | 4/1991 | Kheiri ................. G01N 33/521 422/401 |
| 5,110,555 | A | * | 5/1992 | Moore ................. B01L 3/0203 141/244 |
| 5,872,713 | A | * | 2/1999 | Douglas ............. A61B 5/14532 204/403.01 |
| 6,375,626 | B1 | * | 4/2002 | Allen ................. A61B 5/14514 600/573 |
| 6,991,940 | B2 | | 1/2006 | Carroll et al. |
| 7,049,130 | B2 | | 5/2006 | Carroll et al. |

(Continued)

OTHER PUBLICATIONS

International Search Report and Written Opinion of International Application No. PCT/US2012/041279 dated Aug. 14, 2012.

*Primary Examiner* — Christine T Mui
*Assistant Examiner* — Emily R. Berkeley
(74) *Attorney, Agent, or Firm* — Kyle D. Petaja

(57) ABSTRACT

A test device for analyzing fluid samples. The test device includes a planar support member for supporting reagent pads, and a handle attached to, or for attaching to the planar support member. The test device can be treated with a fluid sample by disposing a fluid sample on the reagent pads. The fluid sample can be disposed onto the reagent pads by the handle, or by dipping the test device into the fluid sample.

10 Claims, 8 Drawing Sheets

(56) References Cited

U.S. PATENT DOCUMENTS

| | | | |
|---|---|---|---|
| 2001/0028862 A1 | 10/2001 | Iwata et al. | |
| 2005/0119589 A1* | 6/2005 | Tung | A61B 10/0045 600/584 |
| 2008/0058676 A1 | 3/2008 | Yong | |

* cited by examiner

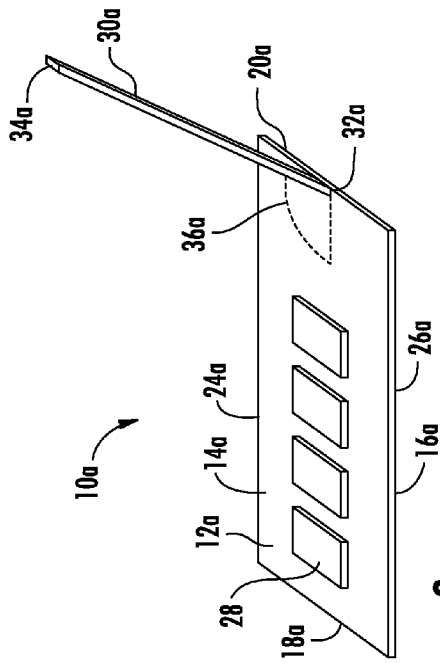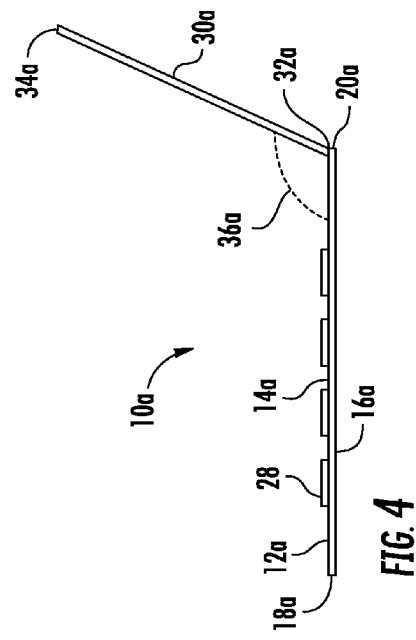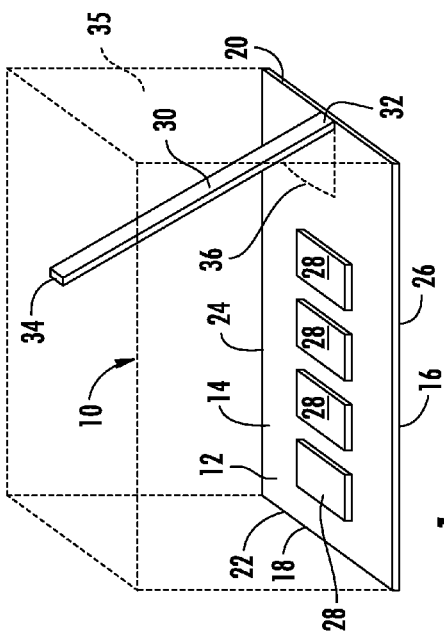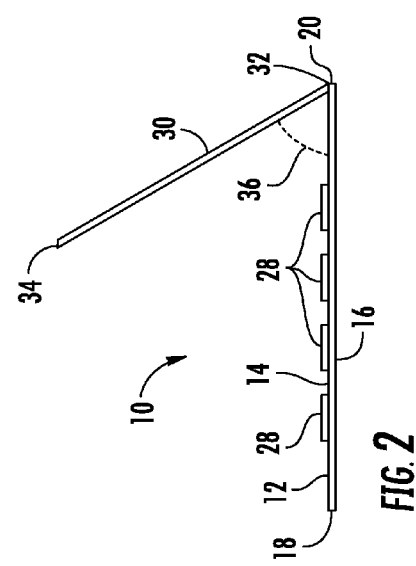

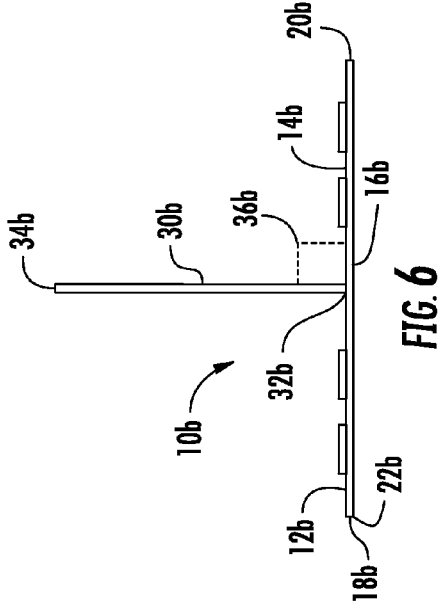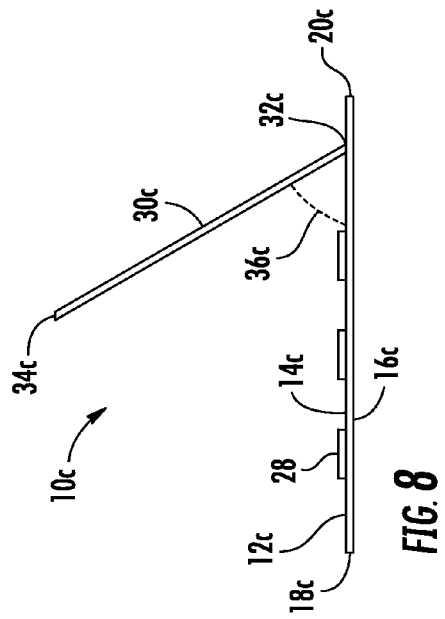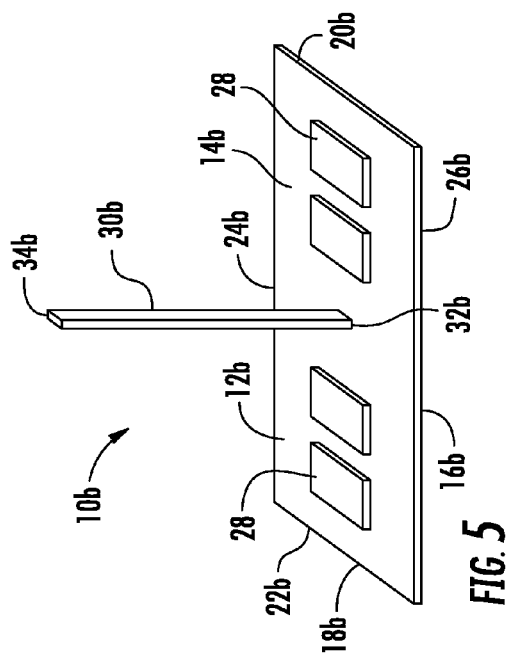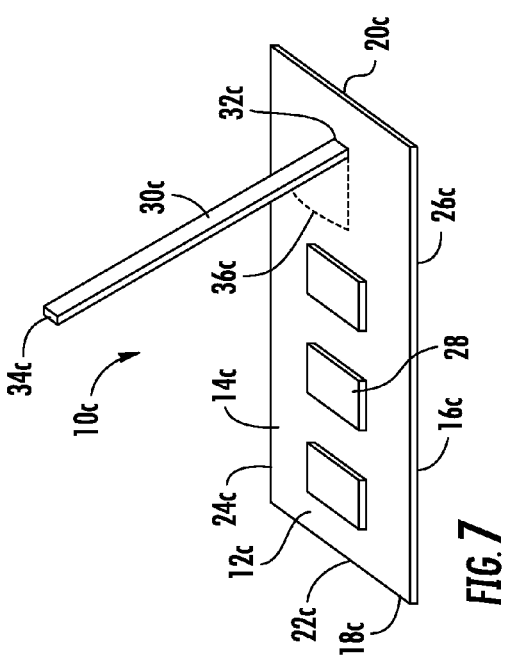

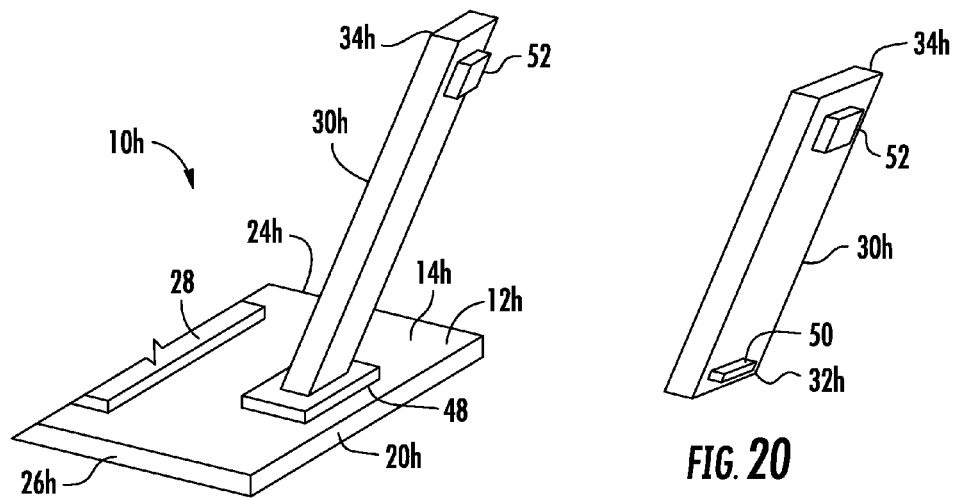
FIG. 19
FIG. 20
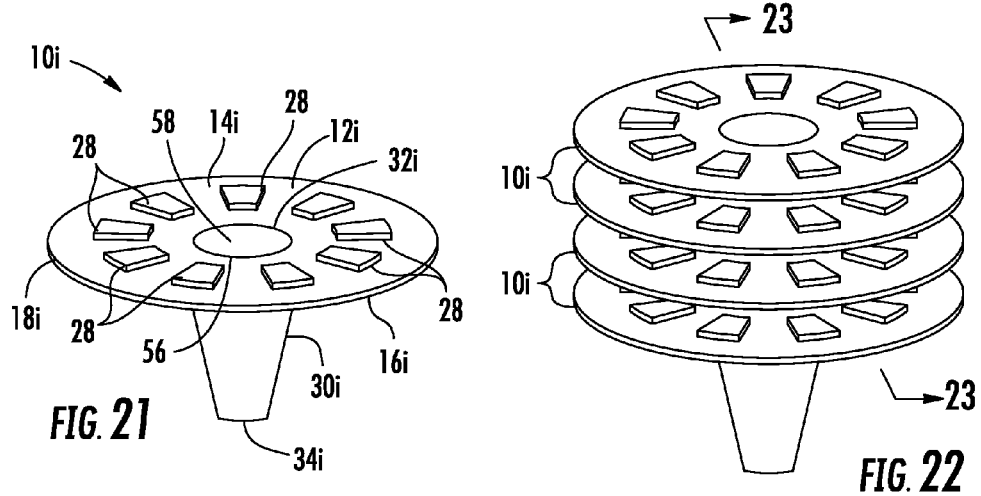
FIG. 21
FIG. 22
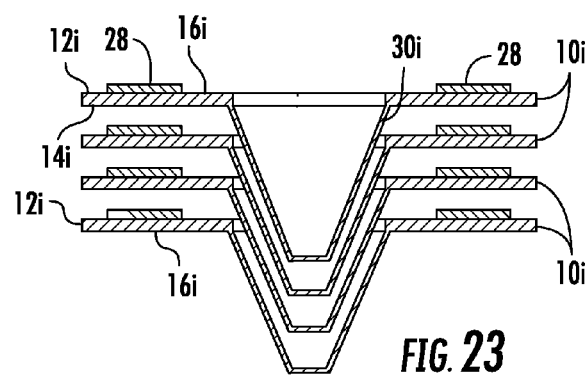
FIG. 23

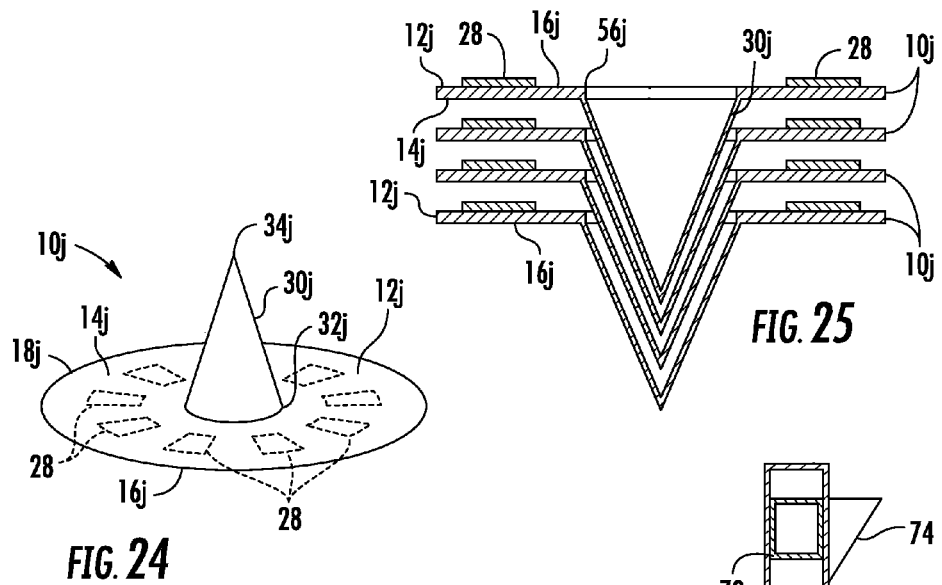
FIG. 24
FIG. 25
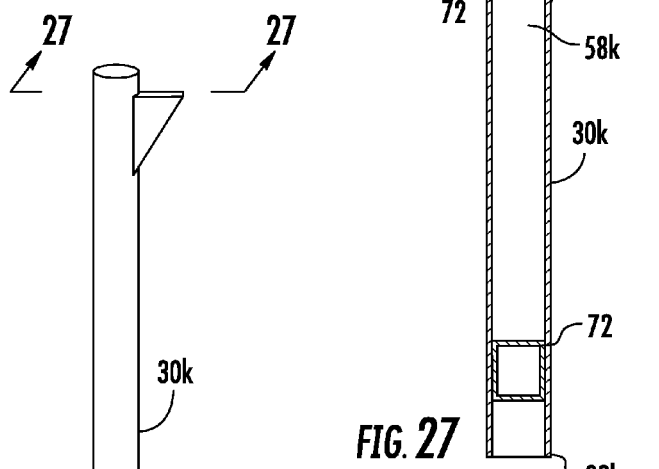
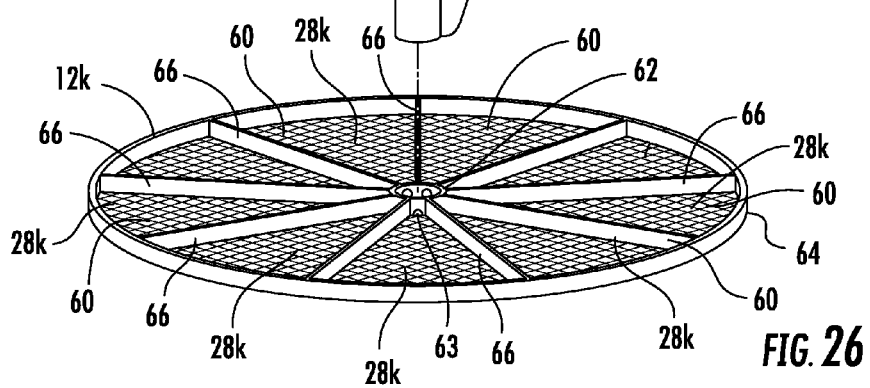
FIG. 26
FIG. 27

TEST DEVICE AND METHODS OF USE

CROSS REFERENCE TO RELATED APPLICATIONS

This application claims benefit under 35 U.S.C. 119(e) of provisional application U.S. Ser. No. 61/498,076, filed Jun. 17, 2011, the entire contents of which are hereby expressly incorporated herein by reference.

BACKGROUND OF THE PRESENTLY DISCLOSED AND/OR CLAIMED INVENTIVE CONCEPTS

1. Field of the Presently Disclosed and/or Claimed Inventive Concepts

The inventive concepts disclosed and claimed herein relate to devices and systems for collecting and analyzing fluid samples, and more particularly, but not by way of limitation, to a fluid test device having a handle and a method of using same.

2. Brief Description of Related Art

Test strips provided with one or more reagents therein or having one or more reagent test pads disposed thereon are conventionally known testing devices which are often used to determine whether a sufficient concentration of one or more chemicals is present in a solution. In the conventionally known procedures, the test strip having reagent chemicals disposed thereon is placed in contact with a solution to be tested, typically by dipping the test strip in the solution, or by wetting the test strip with a sample of a solution. When the test strip is sufficiently wetted, it is removed from the solution and the indication on the test strip is examined after a predetermined waiting time. The test strip may be designed to change to a particular color or range of colors corresponding to the concentration of the chemicals in the solution being examined or to emit a particular electromagnetic wavelength when irradiated which is correlated to the amount or concentration of the analyte in the solution.

The test strips may be analyzed using methods known in the art. For example, the test strips may be analyzed by exposing the reagent test pads to a spectrophotometer or other analyzer or device able to detect changes in color or other wavelengths which are reflected or emitted from the reagent test pads of the test strip.

In some types of testing, a sample or specimen from the subject to be tested is collected within a reservoir in a container such as a cup. The test strip is then deposited or dipped into sample within the container to expose the reagent test pads to the sample. It is often difficult to dip or submerge the test strip within the sample container because the test strips must themselves be grasped by the user, rendering them susceptible to being dropped and lost in the sample container or causing the fingers of the user to touch the sample within the container or by causing uneven application of the fluid to the test strip. To this end, a need exists for a test device that is easier to handle, improves sample collection and even distribution of the sample, and is less prone to being mishandled or lost.

BRIEF DESCRIPTION OF THE DRAWINGS

FIG. 1 is a perspective view of a test device constructed in accordance with the presently disclosed inventive concepts.

FIG. 2 is a side view of the test device of FIG. 1.

FIG. 3 is a perspective view of another test device constructed in accordance with the presently disclosed inventive concepts.

FIG. 4 is a side view of the test device of FIG. 3.

FIG. 5 is a perspective view of another test device constructed in accordance with the presently disclosed inventive concepts.

FIG. 6 is a side view of the test device of FIG. 5.

FIG. 7 is a perspective view of another test device constructed in accordance with the presently disclosed inventive concepts.

FIG. 8 is a side view of the test device of FIG. 7.

FIG. 19 is a perspective view of a test device similar to that of FIGS. 17 and 18, but wherein the handle can be attached to the dock by a releasable attaching element.

FIG. 20 is a perspective view of a handle for use with the test device of FIG. 19.

FIG. 21 is a perspective view of another test device constructed in accordance with the presently disclosed inventive concepts.

FIG. 22 is a perspective view of a plurality of the test devices of FIG. 21 shown nested with one another.

FIG. 23 is a cross-sectional view taken along line 23-23 of FIG. 22.

FIG. 24 is a perspective view of another test device constructed in accordance with the presently disclosed inventive concepts.

FIG. 25 is a side cross-sectional view of a plurality of the test devices of FIG. 24 shown nested with one another.

FIG. 26 is a perspective view of another test device constructed in accordance with the presently disclosed inventive concepts indicating an unattached handle in a position above the test device.

FIG. 27 is a cross-sectional view of the handle of the test device of FIG. 26.

DETAILED DESCRIPTION OF EXEMPLARY EMBODIMENTS

Figure 9:
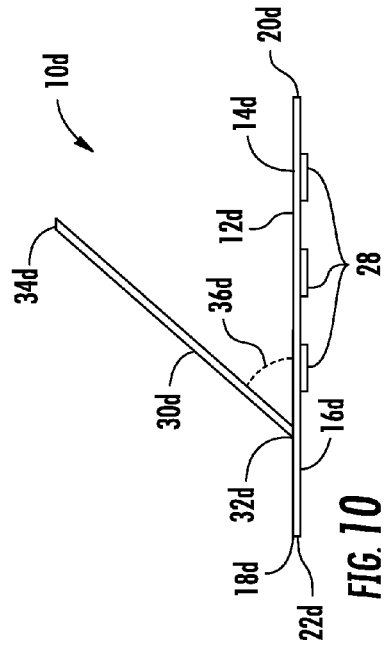
FIG. 9 is a perspective view of another test device constructed in accordance with the presently disclosed inventive concepts.

Before explaining at least one embodiment of the presently disclosed and claimed inventive concept(s) in detail, it is to be understood that the presently disclosed and claimed inventive concept(s) is not limited in its application to the details of construction, experiments, exemplary data, and/or the arrangement of the components set forth in the following description or illustrated in the drawings. The presently disclosed and claimed inventive concept(s) is capable of other embodiments or of being practiced or carried out in various ways. Also, it is to be understood that the phraseology and terminology employed herein is for purpose of description and should not be regarded as limiting.

As noted below, the test devices disclosed herein utilize one or more reagents positioned or disposed thereon or therein, often deposited upon a reagent substrate or pad (also referred to herein as a reagent pad or test pad) which is positioned on and affixed to a support member of the test device. There are various reagents which could be used in the reagent pads (or the discrete reagent areas) of the test devices of the presently disclosed inventive concepts. Reagents in the reagent pads undergo changes whereby the intensity of the signal generated is proportional to the concentration of the analyte measured in a clinical sample. Reagents which can be used include, but are not limited to, indicator dyes, metals, enzymes, polymers, antibodies, electrochemically reactive ingredients and various other chemicals deposited onto the reagent pads which are often constructed from materials including, but not limited to, papers, membranes or polymers with various sample uptake and transporting properties. They can be placed on or in the test devices of the presently disclosed inventive concepts. The reagent pads on the test device may be equally spaced in a radial or linear array and each maybe configured to receive a portion of a single sample, as described above. Test devices of the presently disclosed inventive concepts may use only one reagent pad or reagent area to contain all chemicals needed to generate a color response to the analyte. Typical chemical reactions occurring in the reagent pads of the test devices disclosed herein, include but are not limited to, dye binding, enzymatic, immunological, nucleotide, oxidation or reductive chemistries. As such reagents and chemical reactions are well known to persons having ordinary skill in the art, further discussion of them herein is not included herein.

In some cases, more than one competing and timed chemical reaction may be occurring within one or more reagent pads in the test device. A method for detecting blood in urine is an example of multiple chemical reactions occurring in a single test device. For example, the analyte detecting reaction is based on the peroxidase-like activity of hemoglobin that catalyzes the oxidation of an indicator, 3,3',5,5'-tetramethyl-benzidine, by diisopropylbenzene dihydroperoxide. In the same reagent pad, a second reaction may occur to remove ascorbic acid interference, based on the catalytic activity of a ferric-HETDA complex that catalyzes the oxidation of ascorbic acid by diisopropylbenzene dihydroperoxide.

Described herein and shown in the accompanying drawings are several non-limiting embodiments of test devices of the presently disclosed inventive concepts which may be used for analyzing a liquid sample. Preferably the liquid sample is from a biological source as described in further detail below. A "liquid" refers to any substance in a fluid state having no fixed shape but a substantially fixed volume. The liquid may be homogeneous or heterogeneous.

Referring to FIGS. 1 and 2, a test device of the presently disclosed inventive concepts, designated therein by the general reference numeral 10 is shown. The test device 10 includes a planar support member 12 which has a top surface 14, a bottom surface 16, an outer peripheral edge 18, a first end 20, a second end 22, a first side 24, and a second side 26. The planar support member 12 can be formed of any suitable material which is rigid or semi-rigid and which is non-reactive with the reagents present in the reagent pads to be described below and the fluid sample to be tested. The thickness of the planar support member 12 may vary. In addition, the planar support member 12 may have hydrophobic properties. The planar support member 12 may be formed of a single layer of material or multiple layers of material, the planar support member 12 may be molded or embossed cartridges which may be in the form of microfluidic devices. Examples of suitable materials for use in forming the planar support member 12 include polyethylene terephthalate, polysytrene, polyester, polyethylene polypropylene, nylon, polyvinylidene chloride, polyvinyl chloride, multi-resin, and ethylene vinyl alcohol.

In the embodiment illustrated in FIGS. 1 and 2, the planar support member 12 is formed in the shape of rectangular strip. However, the size and the shape of the planar support member 12 may be varied, as desired. For example, the planar support member 12 may be formed to be circular in shape.

The test device 10 has a plurality of reagent pads 28 disposed on the top surface 14 (or alternately on the bottom surface 16). The exemplary test device 10 is shown as having four reagent pads 28 but it will be understood by a person having ordinary skill in the art that any number of reagent pads 28 may be placed on the planar support member 12 of the test device 10. The reagent pads 28 may be disposed directly upon the top surface 14, or the reagent pad 28 may comprise a discrete area of the top surface 14 in which a reagent has been directly disposed into the planar support member 12 without first being put onto a separate pad material.

The test device 10 further provided with a handle 30 which has a first end 32 and a second end 34. The first end 32 of the handle 30 is attached to a portion of the planar support member 12, for example to the top surface 14 or to the outer peripheral edge 18. The second end 34 is left free and extends away from the planar support member 12. In FIGS. 1 and 2, the handle 30 is shown as attached to the top surface 14 in a position adjacent to the outer peripheral edge 18. The handle 30 extends over the top surface 14 at an angle 36 between the planar support member 12 and the handle 30. The angle 36 is greater than 0° and less than or equal to 90° such that the handle 30 is disposed within a zone bounded by an imaginary plane 35 extending perpendicular from the planar support member 12 at the peripheral edge 18 of the planar support member 12.

FIGS. 3 and 4 illustrate another embodiment of a test device 10a. The test device 10a includes a planar support member 12a which has a top surface 14a, a bottom surface 16a, an outer peripheral edge 18a, a first end 20a, a second end 22a, a first side 24a, and a second side 26a. The test device 10a has a plurality of reagent pads 28 disposed on the top surface 14a (or alternatively on the bottom surface 16a). The exemplary test device 10a is shown as having four reagent pads 28 but it will be understood by a person having ordinary skill in the art that any number of reagent pads 28 may be placed on the planar support member 12a of the test device 10a. The reagent pads 28 may be disposed directly upon the top surface 14a, or the reagent pad 28 may comprise a discrete area of the top surface 14a in which a reagent has been directly disposed into the planar support member 12a without first being put onto a separate pad material.

The test device 10a has a handle 30a which has a first end 32a and a second end 34a. The first end 32a of the handle 30a is attached to a portion of the top surface 14a of the planar support member 12a. The second end 34a is left free and extends away from the planar support member 12a. In FIGS. 3 and 4 the handle 30a is shown as attached to the top surface 14a at a position adjacent to the outer peripheral edge 18a. The handle 30a extends over the top surface 14a at an angle 36a between the planar support member 12a and the handle 30a. The angle 36a is greater than 90° such that the handle 30a extends beyond the outer peripheral edge 18a over the top surface 14a.

Shown in FIGS. 5 and 6 is another embodiment of a test device designated therein by the general reference numeral 10b. The test device 10b includes a planar support member 12b which has a top surface 14b, a bottom surface 16b, an outer peripheral edge 18b, a first end 20b, a second end 22b, a first side 24b, and a second side 26b. The test device 10b has a plurality of reagent pads 28 disposed on the top surface 14b. The test device 10b is shown as having four reagent pads 28 disposed pairwise about handle 30b but it will be understood by a person having ordinary skill in the art that any number of reagent pads 28 may be placed on the planar support member 12b of the test device 10b. The reagent pads 28 may be disposed directly upon the top surface 14, or the reagent pad 28 may comprise a discrete area of the top surface 14 in which a reagent has been directly disposed into the planar support member 12b without first being put onto a separate pad material.

The test device 10b has a handle 30b which has a first end 32b and a second end 34b. The first end 32b of the handle 30b is attached to a central portion of the top surface 14b of the top surface 14b of the planar support member 12b. The second end 34b is left free and extends away from the planar support member 12b. In FIGS. 5 and 6 the handle 30b is shown as attached to a central portion of the top surface 14. The handle 30b extends above the top surface 14b at an angle 36b between the planar support member 12b and the handle 30b. The angle 36b is approximately 90° such that the handle 30b extends perpendicularly from the top surface 14b.

Shown in FIGS. 7 and 8 is another embodiment of a test device designated by the general reference numeral 10c. The test device 10c has a planar support member 12c which has a top surface 14c, a bottom surface 16c, an outer peripheral edge 18c, a first end 20c, a second end 22c, a first side 24c, and a second side 26c. The test device 10c has a plurality of reagent pads 28 disposed on the top surface 14c. The exemplary test device 10c is shown as having three reagent pads 28 but it will be understood by a person having ordinary skill in the art that any number of reagent pads 28 may be placed on the planar support member 12c of the test device 10c. The reagent pads 28 may be disposed directly upon the top surface 14c, or the reagent pad 28 may comprise a discrete area of the top surface 14c in which a reagent has been directly disposed into the planar support member 12c without first being put onto a separate pad material.

The test device 10c has a handle 30c which has a first end 32c and a second end 34c. The first end 32c of the handle 30c is attached to a portion of the top surface 14c of the planar support member 12c. The second end 34c is left free and extends away from the planar support member 12c. In FIGS. 7 and 8 the handle 30c is shown as attached to the top surface 14c at a location interior to the outer peripheral edge 18c. The handle 30c extends over the top surface 14c at an angle 36c between the planar support member 12c and the handle 30c. The angle 36c is greater than 0° and less than or equal to 90° such that the handle 30c is disposed within a zone bounded by an imaginary plane extending perpendicular from the planar support member 12c at the peripheral edge 18c of the planar support member 12c.

Figure 10:
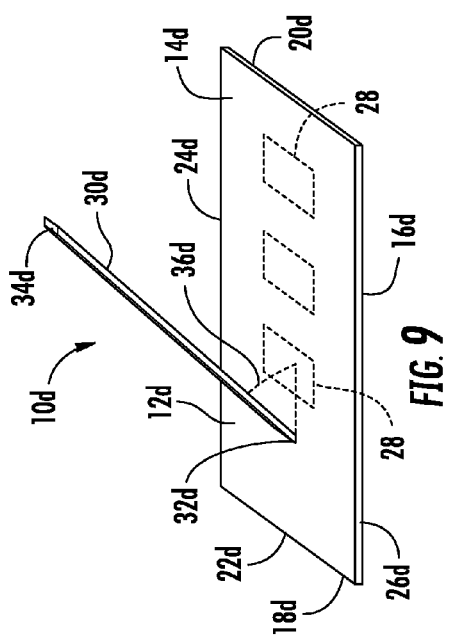
FIG. 10 is a side view of the test device of FIG. 9.

Shown in FIGS. 9 and 10 is another embodiment of a test device designated by the general reference numeral 10d. The test device 10d includes a planar support member 12d which has a top surface 14d, a bottom surface 16d, an outer peripheral edge 18d, a first end 20d, a second end 22d, a first side 24d, and a second side 26d. The test device 10d has a plurality of reagent pads 28 disposed on the bottom surface 16d. The exemplary test device 10d is shown as having three reagent pads 28 but it will be understood by a person having ordinary skill in the art that any number of reagent pads 28 may be placed on the planar support member 12d of the test device 10d. The reagent pads 28 may be disposed directly upon the bottom surface 16d, or the reagent pad 28 may comprise a discrete area of the bottom surface 16d in which a reagent has been directly disposed into the planar support member 12d without first being put onto a separate pad material.

The test device 10d has a handle 30d which has a first end 32d and a second end 34d. The first end 32d of the handle 30d is attached to a portion of the top surface 14d of the planar support member 12d. The second end 34d is left free and extends away from the planar support member 12d. In FIGS. 9 and 10 the handle 30d is shown as attached to the top surface 14d at a location interior to the outer peripheral edge 18d. The handle 30d extends over the top surface 14d at an angle 36d between the planar support member 12d and the handle 30d. The angle 36d is greater than 0° and less than or equal to 90° such that the handle 30d is disposed within a zone bounded by an imaginary plane extending perpendicular from the planar support member 12d at the peripheral edge 18d of the planar support member 12d.

Figure 11:
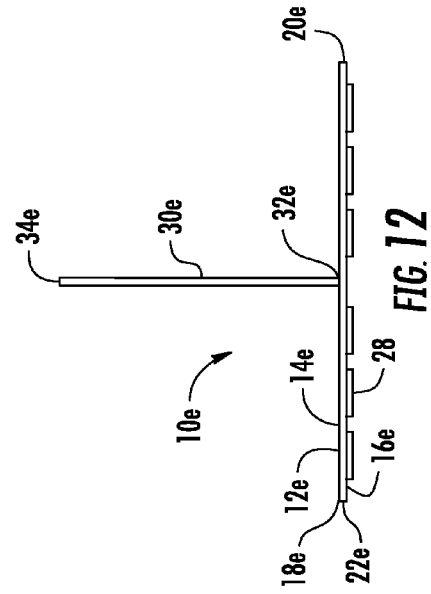
FIG. 11 is a perspective view of another test device constructed in accordance with the presently disclosed inventive concepts.
Figure 12:
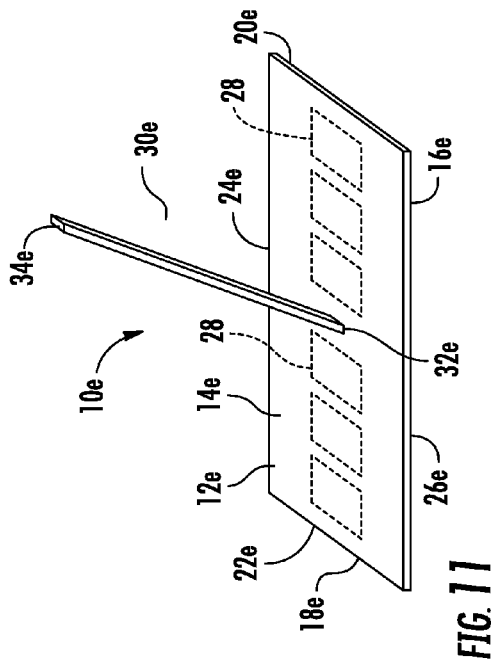
FIG. 12 is a side view of the test device of FIG. 11.
Figure 13:
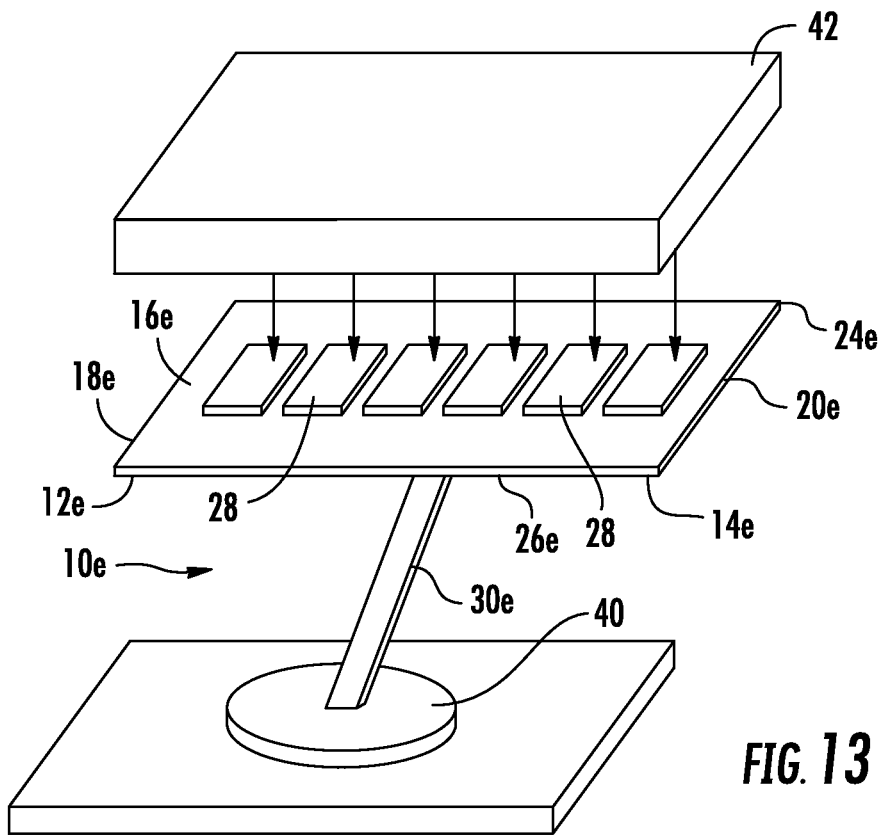
FIG. 13 is a perspective view of the test device of FIG. 11 installed for analysis by a test device analyzer.

Shown in FIGS. 11-13 is an embodiment of a test device 10e which is adapted to be used with an analyzer 42. The test device 10e includes a planar support member 12e which has a top surface 14e, a bottom surface 16e, an outer peripheral edge 18e, a first end 20e, a second end 22e, a first side 24e, and a second side 26e. The test device 10e has a plurality of reagent pads 28 disposed on the bottom surface 16e. The exemplary test device 10e is shown as having six reagent pads 28 but it will be understood by a person having ordinary skill in the art that any number of reagent pads 28 may be placed on the planar support member 12e of the test device 10e. The reagent pads 28 may be disposed directly upon the bottom surface 16e, or the reagent pad 28 may comprise a discrete area of the bottom surface 16e in which a reagent has been directly disposed into the planar support member 12e without first being put onto a separate pad material.

The test device 10e has a handle 30e which has a first end 32e and a second end 34e. The first end 32e of the handle 30e is attached to a portion of the top surface 14e of the planar support member 12e, for example to the top surface 14e or to the outer peripheral edge 18e. The second end 34e is left free and extends away from the planar support member 12e.

The handle 30e is constructed so that the second end 34e can be inserted into an analyzer handle support 40 which positions the bottom surface 16e of the test device 10e adjacent to a sensing portion of a test device analyzer 42 so that the reagent pads 28 on the bottom surface 16e can be analyzed by the test device analyzer 42. The handle 30 extends over the top surface 14e at an angle between the planar support member 12e and the handle 30e. The angle may be greater than 0° and less than or equal to 90°, or greater than 90°.

Figure 14:
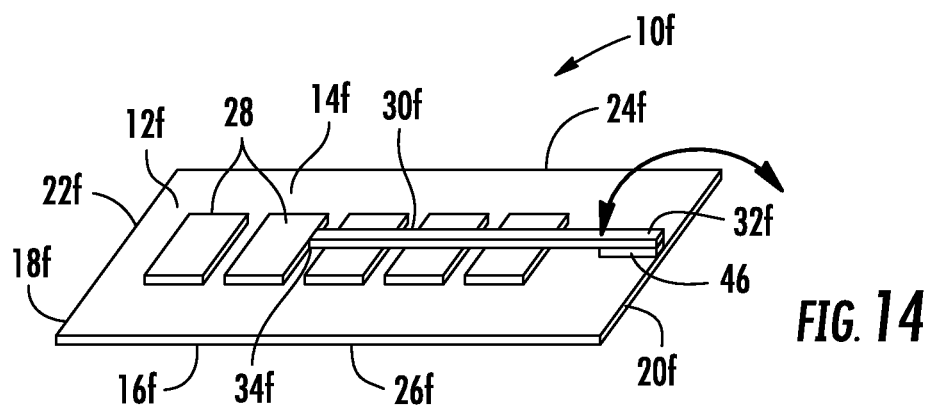
FIG. 14 is a perspective view of another test device constructed in accordance with the presently disclosed inventive concepts.
Figure 15:
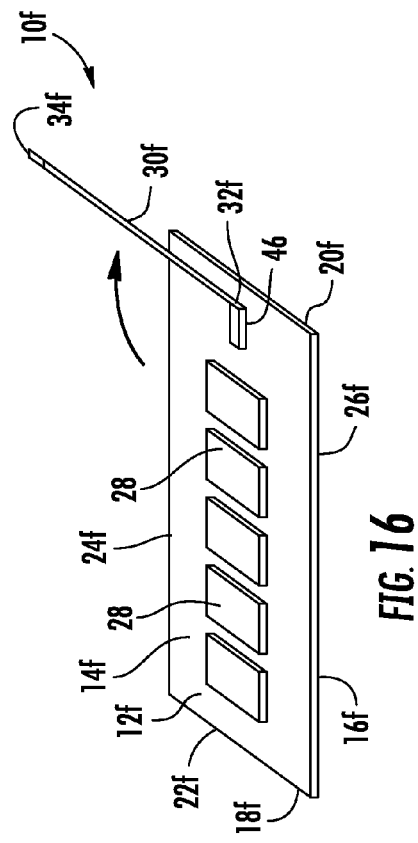
FIG. 15 is a perspective view of the test device of FIG. 14 with the handle partially erected to an angle <90°.
Figure 16:
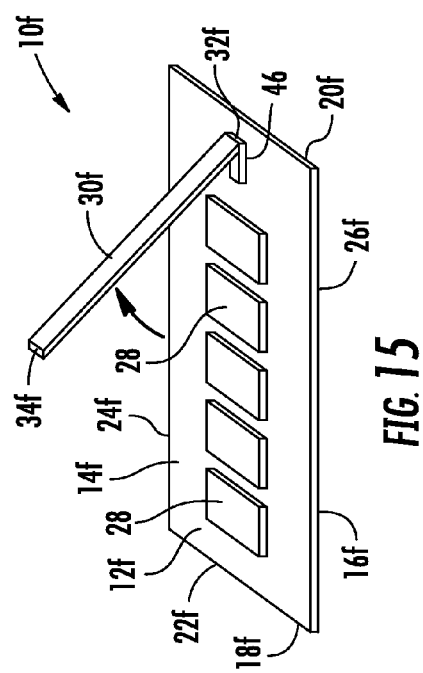
FIG. 16 is a perspective view of the test device of FIG. 14 with the handle erected to an angle >90°.

Shown in FIGS. 14-16 is an another embodiment of a test device designated by the general reference numeral 10f. The test device 10f has a planar support member 12f which has a top surface 14f, a bottom surface 16f, an outer peripheral edge 18f, a first end 20f, a second end 22f, a first side 24f, and a second side 26f. The test device 10f has a plurality of reagent pads 28 disposed on the top surface 14f. The exemplary test device 10f is shown as having five reagent pads 28 but it will be understood by a person having ordinary skill in the art that any number of reagent pads 28 may be placed on the planar support member 12f of the test device 10f. The reagent pads 28 may be disposed directly upon the top surface 14f (or alternatively on the bottom surface 16f), or the reagent pad 28 may comprise a discrete area of the top surface 14f (or alternatively on the bottom surface 16f) in which a reagent has been directly disposed into the planar support member 12f without first being put onto a separate pad material.

The test device 10f has a handle 30f which has a first end 32f and a second end 34f. The first end 32f of the handle 30f is attached to a hinge 46 which is attached to a portion of the planar support member 12f, for example to the top surface 14f or to the outer peripheral edge 18f. The second end 34f is left free and extends away from the planar support member 12f. In FIGS. 14-16, the handle 30f is shown as attached to the top surface 14f at a location interior to the outer peripheral edge 18f. The handle 30f extends over the top surface 14f at an angle 36f between the planar support member 12f and the handle 30f which can range from 0° in storage position, to 90°, to greater than 90° such that the handle 30f is disposed within a zone bounded by an imaginary plane extending perpendicular from the planar support member at the peripheral edge of the planar support member. In this embodiment, the test device 10f can be easily stored and shipped with the handle 30f attached thereto with the handle 30f positioned flat upon the planar support member 12f.

Figure 17:
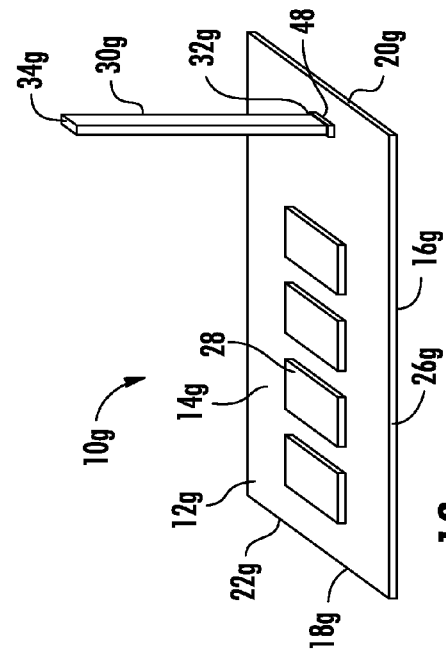
FIG. 17 is a perspective view of another test device constructed in accordance with the presently disclosed inventive concepts.
Figure 18:
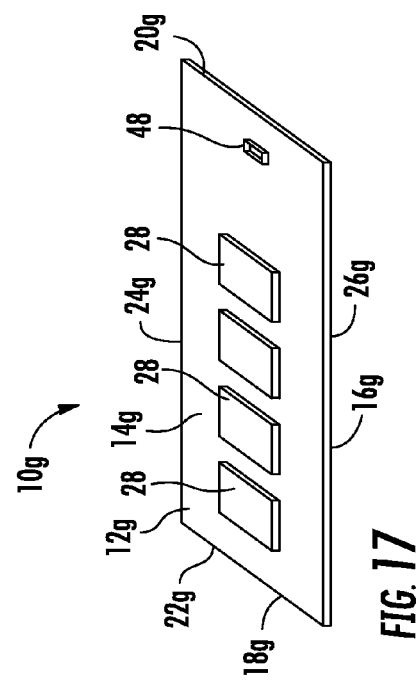
FIG. 18 is a perspective view of the test device of FIG. 17 with a handle attached thereto.
Figure 28:
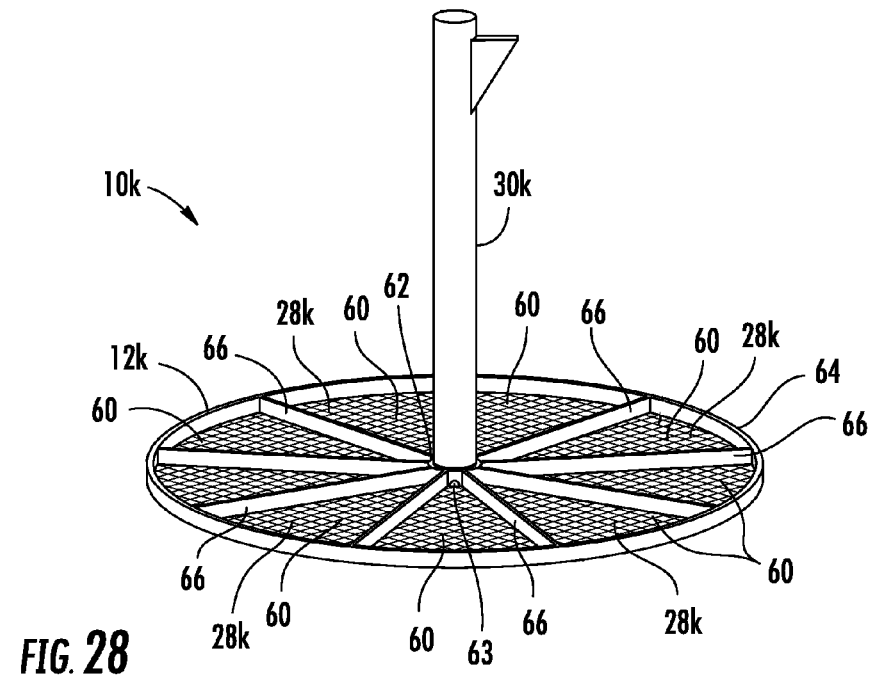
FIG. 28 is a perspective view of the test device of FIG. 26 with the handle attached thereto.
Figure 29:
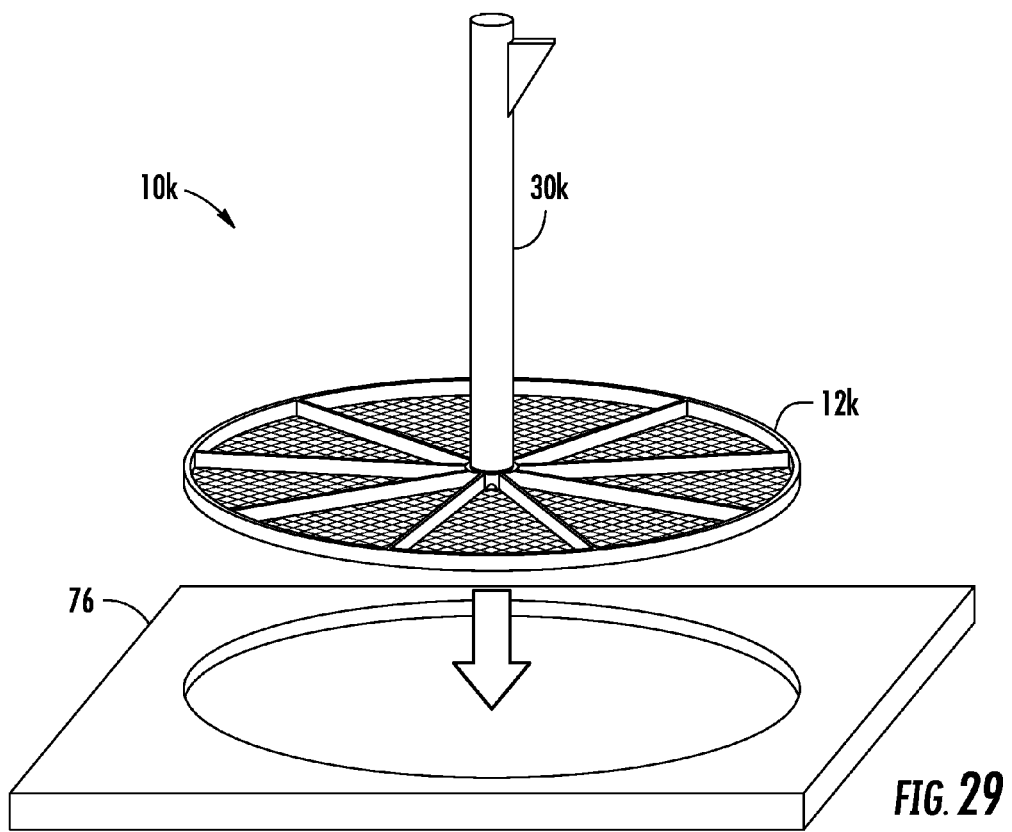
FIG. 29 is a perspective view of the test device of FIG. 28 in a position above an analysis position of an analyzer.

Shown in FIGS. 17-18 is an embodiment of a test device 10g that includes a handle which is separate and attachable and optionally detachable. The test device 10g hasf a planar support member 12g which has a top surface 14g, a bottom surface 16g, an outer peripheral edge 18g, a first end 20g, a second end 22g, a first side 24g, and a second side 26g. The test device 10g has a plurality of reagent pads 28 disposed on the top surface 14g. The test device 10g is shown as having four reagent pads 28 but it will be understood by a person having ordinary skill in the art that any number of reagent pads 28 may be placed on the planar support member 12g of the test device 10g. The reagent pads 28 may be disposed directly upon the top surface 14g (or the bottom surface 16g), or the reagent pad 28 may comprise a discrete area of the top surface 14g (or the bottom surface 16g) in which a reagent has been directly disposed into the planar support member 12g without first being put onto a separate pad material.

The test device 10g has a handle 30g which has a first end 32g and a second end 34g. The first end 32g of the handle 30g is attachable to a portion of the planar support member 12g, for example to the top surface 14g (or bottom surface 16g) or to the outer peripheral edge 18g. The handle 30g may extend over the top surface 14g (or bottom surface 16g) at an angle between the planar support member 12g and the handle 30g at an angle which is greater than 0° and less than or equal to 90° such that the handle 30g is confined within the bounds of the outer peripheral edge 18g in the space above the top surface 14g, or it may be greater than 90° such that it extends beyond the outer peripheral edge 18g.

The test device 10g has a handle 30g which is initially separate from the planar support member 12g. The first end 32g can be inserted into a handle dock 48 on the top surface 14g of the planar support member 12g (as shown) or on the bottom surface 16g (not shown), or on both the top surface 14g and bottom surface 16g. The handle dock 48 can be constructed such that the handle 30g, once inserted therein and held frictionally therein, can have any of the angles (≤90° or >90°) contemplated elsewhere herein and may be constructed so that the handle 30g is removable from the handle dock 48 or is non-removable from the handle dock 48. For example, the handle 30g may be "snapped" or "locked" into position in the handle dock 48 and held thereto in a non-detachable configuration.

Shown in FIGS. 19 and 20 is another embodiment of a test device 10h that has a handle which is constructed to be both attachable and detachable and have an engaging element on the handle. The test device 10h has a planar support member 12h which has a top surface 14h, a bottom surface 16h, an outer peripheral edge 18h, a first end 20h, a second end 22h, a first side 24h, and a second side 26h. The test device 10h has a plurality of reagent pads 28 disposed on the top surface 14h (or bottom surface 16h). The exemplary test device 10h is shown as having one or more reagent pads 28 but it will be understood by a person having ordinary skill in the art that any number of reagent pads 28 may be placed on the planar support member 12h on the test device 10h. The reagent pads 28 may be disposed directly upon the top surface 14h, or the reagent pad 28 may comprise a discrete area of the top surface 14h in which a reagent has been directly disposed into the planar support member 12h without first being put onto a separate pad material.

The test device 10h has a handle 30h which has a first end 32h and a second end 34h. The handle 30h is initially separate from the planar support member 12h, which has a handle dock 48 positioned on the top surface 14h (or alternatively on the bottom surface 16h, or docks 48 on both the top surface 14h and bottom surface 16h). The handle 30h has an engagement tab 50 which is near the first end 32h of the handle 30h, and a release mechanism 52 which is shown as located at or near the first end 32h of the handle 30h, but which may be located at any convenient position of the handle 30h in a manner familiar to persons having ordinary skill in the art. When the first end 32h of the handle 30h is inserted into the handle dock 48, the engagement tab 50 engages the handle dock 48 to secure the handle 30h thereto. The handle 30h can then be detached from the handle dock 48, when desired by the user by pressing on the release mechanism 52 which causes the engagement tab 50 to be disengaged from the handle dock 48. When attached, the handle 30h extends over the top surface 14h at an angle between the planar support member 12h and the handle 30h wherein the angle may be greater than 0° and less than or equal to 90°, such that the handle 30h is disposed within a zone bounded by an imaginary plane extending perpendicular from the planar support member 12h at the peripheral edge 18h of the planar support member 12h, or may extend beyond the bounds of the outer peripheral edge 18h wherein the angle is >90°.

Referring now to FIGS. 21-23, an embodiment of a test device 10i is shown. The test device 10i includes a planar support member 12i which has a top surface 14i, a bottom surface 16i, and a curved outer peripheral edge 18i. The test device 10i has a plurality of reagent pads 28 disposed on the top surface 14*i*. The exemplary test device 10*i* is shown as having a plurality of reagent pads 28 but it will be understood by a person having ordinary skill in the art that any number of reagent pads 28 may be placed on the planar support member 12*i* of the test device 10*i*. The reagent pads 28 may be disposed directly upon the top surface 14*i*, or the reagent pad 28 may comprise a discrete area of the top surface 14*i* in which a reagent has been directly disposed into the planar support member 12*i* without first being put onto a separate pad material.

The test device 10*i* has a hollow handle 30*i* which has a first end 32*i* and a second end 34*i*. The first end 32*i* of the handle 30*i* is attached to a central portion of the planar support member 12*i*. The second end 34*i* is left free and perpendicularly extends away from the planar support member 12*i*. The handle 30*i* is tapered from the first end 32*i* to the second end 34*i* so that the test device 10*i* is nestable with another handle 30*i*.

The handle 30*i* is attached at first end 32*i* to the bottom surface 16*i* of the planar support member 12*i* of the test device 10*i* and has a handle aperture 56 which extends through the planar support member 12*i* and into an inner space of the handle 30*i* which is hollow. Because the handle 30*i* is hollow and tapered, a plurality of test devices 10*i* can be stacked together by nesting the hollow handles 30*i* of the test devices 10*i* within each other, as shown in FIGS. 22 and 23.

Shown in FIGS. 24 and 25 is another embodiment of a test device 10*j*. The test device 10*j* includes a planar support member 12*j* which has a top surface 14*j*, a bottom surface 16*j*, and a circular outer peripheral edge 18*j*. The test device 10*j* has a plurality of reagent pads 28 disposed on the top surface 14. The exemplary test device 10*j* is shown as having a plurality of reagent pads 28 but it will be understood by a person having ordinary skill in the art that any number of reagent pads 28 may be placed on the planar support member 12*j* of the test device 10*j*. The reagent pads 28 may be disposed directly upon the top surface 14*j*, or the reagent pad 28 may comprise a discrete area of the top surface 14*j* in which a reagent has been directly disposed into the planar support member 12*j*.

The test device 10*j* has a hollow, conical handle 30*j* which has a first end 32*j* and a second end 34*j*. The first end 32*j* of the handle 30*j* is attached to a central portion of the planar support member 12*j*. In a similar manner to that shown in FIGS. 21-23, a plurality of the test devices 10*j* having conically-shaped hollow handles 30*j* can be nested by inserting the hollow handles 30*j* of a plurality of test devices 10*j* into each other, as shown for example in FIG. 25.

Referring now to FIGS. 26-29, an embodiment of a test kit 10*k* is shown. The test kit 10*k* includes a test device 12*k* and a handle 30*k*. The test device 10*k* comprises a plurality of reagent compartments 60 which radiate from a centrally positioned handle receiving port 62. The handle receiving port 62 is in fluid communication with each reagent compartment 60 via a port 63 provided in the handle receiving port 62. The test device 12*k* comprises an outer wall 64 which comprises the outer walls of each reagent compartment 60 and a plurality of inner walls 66 which radiate from the handle receiving port 62. Adjacent pairs of the inner walls 66 form the inner walls of each reagent compartment 60. The test device 10 may further include a transparent bottom to facilitate analysis of the fluid sample. Each reagent compartment comprises a reagent pad 28*k* disposed therein which can be supplied with a liquid sample from the handle receiving port 62.

The handle 30*k* of test device 10*k* is generally tubular and has an inner space 58*k* for receiving a fluid sample. The handle 30*k* comprises a mechanism which can be employed to draw the fluid sample in the inner space 58*k*. In the embodiment of the test device 10*k*, the mechanism comprises a plunger mechanism 72 which can be actuated by a release mechanism 74 to cause the fluid sample to be drawn into the inner space 58*k* when the first end 32*k* of the handle 30*k* is submerged in a container of fluid, such as a container of urine, plasma, blood, or any other fluid described elsewhere herein or known in the art to be analyzed. The first end 32*k* of the handle 30*k* is then inserted into the handle receiving port 62, at which point the release mechanism 74 can be actuated again by the user to cause the fluid sample to drain from the handle 30*k*, for example by gravity flow, into each of the reagent compartments 60 whereby the reagent pads 28*k* therein are wetted to enable the fluid to react with the reagents therein. After the test device 10*k* has been allowed to incubate for the desired length of time, it is carried by the handle 30*k* and placed on an analyzer 76 for analysis as described elsewhere herein. The handle 30*k* may be detachable from the planar support member 12*k*. Any plunger mechanism or analyzer which functions in accordance with the presently disclosed inventive concepts can be used and many such mechanisms and analyzers are available commercially and are known to persons having ordinary skill in the art.

The test devices disclosed herein may be constructed to have one or more applications. Generally, the test devices 10-10*j* are used by dipping directly into a fluid held into a container, the exception being the test device 10*k* where the handle 30*k* is used to obtain the fluid. Analyses may be carried out on samples of many fluids of biological origin which are fluids or have been fluidized including, but not limited to, blood, urine, bladder wash, saliva, sputum, spinal fluid, intestinal fluid, intraperitoneal fluid, food, blood, plasma, serum, cystic fluids, ascites, sweat, tears, feces, semen, nipple aspirates, and pus. Blood and urine are of particular interest. Also included are processed biological fluids such as milk, juices, wines, beer, and liquors. Fluids of non-biological origin or which may be contaminated, such as water, are also included. Biological samples analyzed herein may be obtained from any biological sample including humans or any other mammal, birds, fish, reptiles, amphibians, insects, crustaceans, marine animals, plants, fungi, algae and microorganisms. The reacted reagent from the test device may be visually or mechanically assayed for the analyte of interest, including for example a protein, a cell, a small organic molecule, or a metal. Examples of such proteins include, but are not limited to, albumin, HbAlc, protease, protease inhibitor, CRP, esterase, PSA, and BNP. Cells which may be analyzed include, but are not limited to, *E. coli, Pseudomonas* sp., white blood cells, red blood cells, *H. pylori, Streptococcus* sp., *Chlamydia* and mononucleosis pathogens. Metals which may be detected include, but are not limited to, iron, manganese, sodium, potassium, lithium, calcium, and magnesium. In certain embodiments, as described above, the test devices are used in analysis of a biological fluid, such as urine, for components therein or aspects thereof, such as, but not limited to, leukocytes, nitrites, urobilinogen, proteins, albumin, creatinine, uristatin, calcium oxalate, myoglobin, pH, blood, specific gravity, ketone, bilirubin and glucose.

In many applications, it is desired to measure a color, light or wavelength emission developed by the reaction of reagents of the test device with the sample fluid and which may be measured or detected by analyzers known to those of ordinary skill in the art. It may also be feasible to make electrical measurements of the sample, using electrodes positioned in the test pads in the strip. Examples of such analyses include electrochemical signal transducers based on amperometric, impedimetric, or potentimetric detection methods. Examples include the detection of oxidative and reductive chemistries and the detection of binding events.

It is contemplated that virtually any reagent used in the field of medical, biological, chemical, or biochemical analyses could be used in the test devices disclosed herein. As noted above, reagents undergo changes whereby the intensity, nature, frequency, or type of the signal generated is proportional to the concentration of the analyte measured in the clinical specimen. These reagents may contain indicator dyes, metals, enzymes, polymers, antibodies, electrochemically reactive ingredients and various other chemicals placed onto carriers (also referred to herein as test pads or reagent substrates). Carriers often used are papers, membranes or polymers with various sample uptake and transport properties. Liquid reagents, when used, are preferably isolated by barrier materials which prevent migration of water throughout the strip or device, thus avoiding changes in the concentration through transpiration or evaporation and preventing moisture from reaching the dry reagents.

Any method of detecting and measuring an analyte in liquid sample can be used in and with the presently disclosed inventive concepts. A variety of assays for detecting analytes are well known in the art and include, but are not limited to, enzyme inhibition assays, antibody stains, latex agglutination, and immunoassays, e.g., radioimmunoassay.

Immunoassays that determine the amount of protein in a biological sample typically involve the development of antibodies against the protein. The term "antibody" herein is used in the broadest sense and refers to, for example, intact monoclonal antibodies, polyclonal antibodies, multispecific antibodies (e.g., bispecific antibodies), and refers to antibody fragments that exhibit the desired biological activity (e.g., antigen-binding). The antibody can be of any type or class (e.g., IgG, IgE, IgM, IgD, and IgA) or sub-class (e.g., IgG1, IgG2, IgG3, IgG4, IgA1 and IgA2).

Immunoassays, including radioimmunoassay and enzyme-linked immunoassays, are useful in the methods of the presently disclosed inventive concepts. A variety of immunoassay formats, including, for example, competitive and non-competitive immunoassay formats, antigen capture assays and two-antibody sandwich assays can be used in the methods of the invention.

Enzyme-linked immunosorbent assays (ELISAs) can be used in the presently disclosed inventive concepts. In the case of an enzyme immunoassay, an enzyme is typically conjugated to the second antibody, generally by means of glutaraldehyde or periodate. As will be readily recognized, however, a wide variety of different conjugation techniques exist which are readily available to one having ordinary skill in the art.

In certain embodiments, the analytes are detected and measured using chemiluminescent detection. For example, in certain embodiments, analyte-specific antibodies are used to capture an analyte present in the biological sample and an antibody specific for the specific antibodies and labeled with a chemiluminescent label is used to detect the analyte present in the sample. Any chemiluminescent label and detection system can be used in the presently disclosed test devices. Chemiluminescent secondary antibodies can be obtained commercially from various sources. Methods of detecting chemiluminescent secondary antibodies are known in the art and are not discussed herein in detail.

Fluorescent detection also can be useful for detecting analytes in the presently disclosed inventive concepts. Useful fluorochromes include, but are not limited to, DAPI, fluorescein, lanthanide metals, Hoechst 33258, R-phycocyanin, B-phycoerythrin, R-phycoerythrin, rhodamine, Texas red and lissamine. Fluorescent compounds, can be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic color visually detectable with a light microscope.

Radioimmunoassays (RIAs) can be useful in certain methods of the invention. Such assays are well known in the art. Radioimmunoassays can be performed, for example, with $^{125}$I-labeled primary or secondary antibody.

Although the presently disclosed inventive concepts and the advantages thereof have been described in detail with reference to certain exemplary embodiments and implementations thereof, it should be understood that various changes, substitutions, alterations, modifications, and enhancements can be made to the presently disclosed inventive concepts described herein without departing from the spirit and scope thereof as defined by the appended claims. Moreover, the scope of the presently disclosed inventive concepts is not intended to be limited to the particular embodiments of the processes, assemblies, items of manufacture, compositions of matter, means, methods and steps described in the specification. As one of ordinary skill in the art will readily appreciate from the present disclosure, many equivalent processes, assemblies, items of manufacture, compositions of matter, means, methods, or steps, presently existing or later to be developed that perform substantially the same function or achieve substantially the same result as the corresponding embodiments described herein may be utilized according to the presently disclosed inventive concepts disclosed and claimed herein. Accordingly, the appended claims are intended to include within their scope all such equivalent processes, assemblies, items of manufacture, compositions of matter, means, methods, or steps.

What is claimed is:

1. A fluid test device, comprising:
a planar support member having a top surface, a bottom surface, and an outer peripheral edge;
one or more reagent pads disposed on the bottom surface of the planar support member in a way that at least a portion of each of the reagent pads extends from a bottommost portion of the bottom surface of the planar support member in a direction away from the top surface; and
a handle extending from the top surface of the planar support member such that the handle is disposed entirely within a zone defined by an area of space extending from an entirety of the outer peripheral edge in a direction perpendicular to the top surface and the bottom surface of the planar support member.

2. The test device of claim 1 wherein the handle is a unitary extension of the planar support member.

3. The test device of claim 1 wherein the handle is an independent member attached to the planar support member.

4. The test device of claim 1 wherein the handle extends perpendicular to the planar support member.

5. The test device of claim 1 wherein the handle is attached to the planar support member at a location interior to the peripheral edge of the planar support member.

6. The test device of claim 1 wherein the planar support member has an opening extending through the planar support member from the top surface to the bottom, and wherein the handle has a longitudinal passage extending from a proximal end of the handle, and wherein the handle extends from the planar support member such that the longitudinal passage of the handle is axially aligned with the opening of the planar support member.

7. The test device of claim 6 wherein the handle is tapered from the proximal end so that the test device is nestable with another test device.

8. The test device of claim 1, wherein the planar support member further includes a hinge, a first end of the handle attached to the hinge.

9. The test device of claim 3, wherein the planar support member further includes a handle dock positioned on the top surface, wherein a first end of the handle is insertable into the handle dock.

10. The test device of claim 9, wherein the handle further includes an engagement tab located near the first end of the handle and a release mechanism located near a second end of the handle, the engagement tab engageable with the handle dock when the first end of the handle is releasably inserted into the handle dock.

* * * * *